(12) United States Patent
Sugimoto et al.

(10) Patent No.: US 8,399,524 B2
(45) Date of Patent: Mar. 19, 2013

(54) ACYL ACIDIC AMINO ACID ESTER

(75) Inventors: Takanori Sugimoto, Kanagawa (JP); Tatsuya Hattori, Kanagawa (JP); Souichirou Ootake, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/239,520

(22) Filed: Sep. 22, 2011

(65) Prior Publication Data

US 2012/0071570 A1    Mar. 22, 2012

Related U.S. Application Data

(63) Continuation of application No. PCT/JP2010/056289, filed on Mar. 31, 2010.

(30) Foreign Application Priority Data

Mar. 31, 2009    (JP) ................................. 2009-086507

(51) Int. Cl.
*A01N 25/00*    (2006.01)
*A61K 47/00*    (2006.01)

(52) U.S. Cl. ..................................................... 514/785

(58) Field of Classification Search .................. None
See application file for complete search history.

(56) References Cited

U.S. PATENT DOCUMENTS

| | | | |
|---|---|---|---|
| 5,153,340 A * | 10/1992 | Ichikawa et al. .............. | 552/509 |
| 6,268,454 B1 | 7/2001 | Song et al. | |
| 2003/0219395 A1 | 11/2003 | Sakuta | |
| 2007/0009458 A1 | 1/2007 | Masuda et al. | |

FOREIGN PATENT DOCUMENTS

| | | |
|---|---|---|
| JP | 50-35119 | 4/1975 |
| JP | 50-158700 | 12/1975 |
| JP | 52-3023 | 1/1977 |
| JP | 4-145097 | 5/1992 |
| JP | 10-182355 | 7/1998 |
| JP | 2001-114647 | 4/2001 |
| JP | 2001-342254 | 12/2001 |
| JP | 2003-113021 | 4/2003 |
| JP | 2009-500393 | 1/2009 |
| WO | WO 2007007251 A1 * | 1/2007 |

OTHER PUBLICATIONS

International Search Report issued in PCT/JP2010/056289 on Jun. 8, 2010.
Written Opinion issued in PCT/JP2010/056289 on Jun. 8, 2010.

* cited by examiner

*Primary Examiner* — Craig Ricci
*Assistant Examiner* — Jared D Barsky
(74) *Attorney, Agent, or Firm* — Oblon, Spivak, McClelland, Maier & Neustadt, L.L.P.

(57) ABSTRACT

Provided is a novel oily material that spreads smoothly upon application and is free from stickiness, and also gives ungreasy and moisturized feeling after application, but does not give friction feeling peculiar to silicone. The invention was completed upon finding that a specific acyl acidic amino acid monosilicone monosterol ester can solve the foregoing problems.

18 Claims, No Drawings

ACYL ACIDIC AMINO ACID ESTER

CROSS REFERENCES TO RELATED APPLICATIONS

This application is a continuation of International Patent Application No. PCT/JP2010/056289, filed on Mar. 31, 2010, and claims priority to Japanese Patent Application No. 2009-086507, filed on Mar. 31, 2009, both of which are incorporated herein by reference in their entireties.

BACKGROUND OF THE INVENTION

1. Field of the Invention

The present invention relates to novel acyl acidic amino acid esters. The invention also relates to oily bases comprising such compounds, cosmetics comprising such oil bases, and processes for producing such compounds, oil bases, and cosmetics.

2. Discussion of the Background

Generally, various esters have been used as the oily raw material for skin and hair cosmetics and external medicine bases. A variety of sterol esters have conventionally been used as oily raw material that has excellent emulsifying performance. While sterol esters also have desirable moisture holding performance, there is a drawback that sterol esters impair the sensory feel of the product when mixed into cosmetics and external medicinal agents.

This problem is addressed in JP-A-3-275697 and Japanese Patent No. 2990624, which disclose long-chain acyl acidic amino acid sterol esters and long-chain acyl neutral amino acid sterol esters, respectively. However, the problem of impaired sensory feel is still present, and the stickiness problem also remains unsolved.

Silicone is generally known as an oil that has light feel. Modified silicones are also known that are produced by introducing various organic functional groups to impart characteristics. One known example of such silicone is the amino acid-introduced silicones (see JP-A-50-35119 and JP-A-50-158700). However, the sensory feel involves the friction feeling peculiar to silicone.

Sterol derivatives produced by binding this type of silicone to sterol that excels in moisture retention are also known (see JP-A-4-145097). However, sensory feel such as stickiness is still inferior, and material that provides excellent sensory feel, such as non-greasy and non-sticky feeling, while maintaining moisture retention is not available.

SUMMARY OF THE INVENTION

Accordingly, it is one object of the present invention to provide novel compounds which provide oily bases spread smoothly upon application and are free from stickiness, and also give ungreasy and moisturized feeling after application, but do not give the friction feeling peculiar to silicones.

It is another object of the present invention to provide novel oily bases which contain such a compound.

It is another object of the present invention to provide novel cosmetics which contain such a compound or oily base.

These and other objects, which will become apparent during the following detailed description, have been achieved by the inventors' discovery of specific acyl acidic amino acid esters.

Specifically, the present invention provides the following aspects.

(1) An acyl acidic amino acid monosilicone monosterol ester of the following general formula (I):

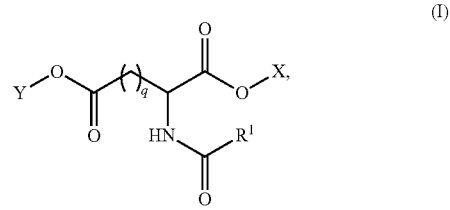

wherein $R^1$ represents a linear or branched hydrocarbon group of 1 to 30 carbon atoms, q is 1 or 2, and one of X and Y is a sterol ester residue, and the other is a silicone ester residue of the following general formula (II):

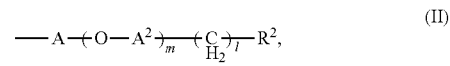

wherein A and $A^2$ are each selected from linear or branched alkylene groups of 1 to 12 carbon atoms; l is an integer of 0 to 2; m is an integer of 0 to 10, and $R^2$ is selected from the general formula (IV) or (V) below:

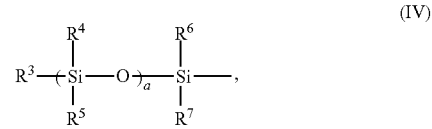

wherein $R^3$, $R^4$, $R^5$, $R^6$, and $R^7$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, a represents a number of from 2 to 10,000,

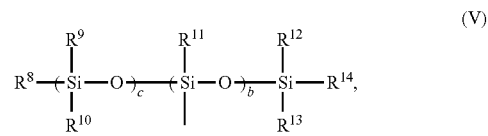

wherein $R^8$, $R^9$, $R^{10}$, $R^{11}$, $R^{12}$, $R^{13}$, and $R^{14}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, c represents a number of from 1 to 10,000, and b represents a number of from 1 to 30.

(2) The acyl acidic amino acid monosilicone monosterol ester of (1), wherein $R^2$ is represented by the general formula (IV).

(3) The acyl acidic amino acid monosilicone monosterol ester of (1) or (2), wherein q=2.

(4) The acyl acidic amino acid monosilicone monosterol ester of any one of (1) to (3), wherein the acyl group represented by $R^1$—CO— is one or more selected from an octanoyl group, a 2-ethylhexanoyl group, a nonanoyl group, a decanoyl group, a lauroyl group, a myristoyl group, a palmitoyl group, a stearoyl group, and an oleoyl group, or one or more selected from acyl groups derived from mixed fatty acids obtained from nature, including coconut oil fatty acid, castor oil fatty acid, olive oil fatty acid, and palm oil fatty acid, or from synthetic fatty acids (including branched fatty acids).

(5) The acyl acidic amino acid monosilicone monosterol ester of any one of (1) to (3), wherein the acyl group represented by $R^1$—CO— is a lauroyl group.

(6) The acyl acidic amino acid monosilicone monosterol ester of (1) to (2), wherein the acyl acidic amino acid monosilicone monosterol ester is lauroylglutamic acid monosilicone monosterol ester.

(7) The acyl acidic amino acid monosilicone monosterol ester of any one of (1) to (6), wherein a is 2 to 100.

(8) A cosmetic, comprising the acyl acidic amino acid monosilicone monosterol ester of any one of (1) to (7).

(9) An oily base, comprising the acyl acidic amino acid monosilicone monosterol ester of any one of (1) to (7).

(10) The oily base of (9), further comprising an acyl acidic amino acid disilicone ester of the following general formula (VIII):

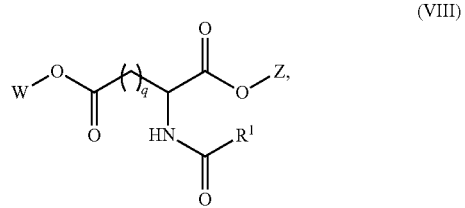

wherein $R^1$ represents a linear or branched hydrocarbon group of 1 to 30 carbon atoms, q is 1 to 2, and Z and W are each independently represented by the following general formula (IX):

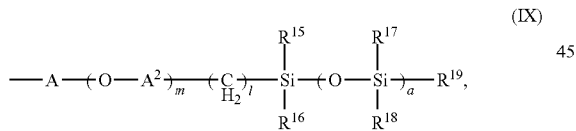

wherein A and $A^2$ are each selected from linear or branched alkylene groups of 1 to 12 carbon atoms; 1 is an integer of 0 to 2; m is an integer of 0 to 10, and $R^{15}$, $R^{16}$, $R^{17}$, $R^{18}$, and $R^{19}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and a represents a number of from 2 to 10,000.

(11) A process for producing a composition that contains an acyl acidic amino acid monosilicone monosterol ester, the process comprising mixing acyl acidic amino acid, carbinol-modified silicone, and sterol, and esterifying the mixture in the presence of an acidic catalyst.

(12) The process of (11), wherein the esterification reaction is performed in the presence of a higher alcohol.

(13) A composition obtained by the process of (11) and (12).

(14) The composition of (13), wherein the composition has a viscosity of 10 to 600 mPa·s.

(15) The composition of (13), wherein the composition has a viscosity of 50 to 500 mPa·s.

(16) An acyl acidic amino acid disilicone ester of the following general formula (VIII):

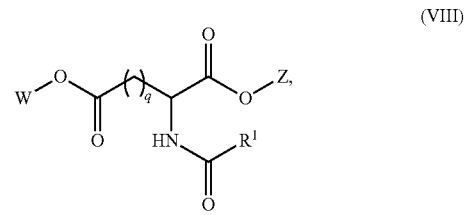

wherein $R^1$ represents a linear or branched hydrocarbon group of 1 to 30 carbon atoms, q is 1 to 2, and Z and W are each independently represented by the following general formula (IX):

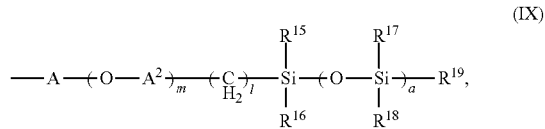

wherein A and $A^2$ are each selected from linear or branched alkylene groups of 1 to 12 carbon atoms; 1 is an integer of 0 to 2; m is an integer of 0 to 10, $R^{15}$, $R^{16}$, $R^{17}$, $R^{18}$, and $R^{19}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and a represents a number of from 2 to 10,000.

The specific acyl acidic amino acid ester of the present invention can provide a novel oily raw material that spreads smoothly upon application and is free from stickiness, and also gives ungreasy and moisturized feeling after application, but does not give friction feeling peculiar to silicone.

DETAILED DESCRIPTION OF THE PREFERRED EMBODIMENTS

The present invention relates to specific acyl acidic amino acid monosilicone monosterol esters.

The acyl acidic amino acid monosilicone monosterol ester of the present invention is a compound in which one of the two carboxylic groups of the acyl acidic amino acid is a silicone ester while the other is a sterol ester.

The acyl acidic amino acid monosilicone monosterol ester of the present invention is represented by the following general formula (I):

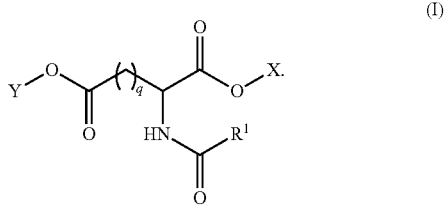

In the formula, $R^1$ represents a linear or branched hydrocarbon group of 1 to 30 carbon atoms. The hydrocarbon group may be linear or branched. The acyl group represented by $R^1$—CO— is an acyl group derived from a saturated or unsaturated fatty acid of 2 to 31 carbon atoms. Preferably, the acyl group is one in which $R^1$ is a linear or branched hydrocarbon group of 7 to 22 carbon atoms, for example, such as an octanoyl group, a 2-ethylhexanoyl group, a nonanoyl group, a decanoyl group, a lauroyl group, a myristoyl group, a palmitoyl group, a stearoyl group, and an oleoyl group. The long-chain acyl group represented by $R^1$—CO— may be an acyl group from fatty acids of the uniform composition, or an acyl group from mixed fatty acids obtained from nature, such as coconut oil fatty acid, castor oil fatty acid, olive oil fatty acid, and palm oil fatty acid, or from fatty acids obtained by synthesis (including branched fatty acids). These may be used alone or as a mixture of two or more selected from the group presented above. From the standpoint of excellent moisturized feeling, one or more selected from the group consisting of a lauroyl group, a myristoyl group, a palmitoyl group, and a stearoyl group is preferable, and a lauroyl group is more preferable.

In the formula, q is 1 or 2, and is preferably 2 from the standpoint of the preservation stability of material.

One of X and Y is a sterol ester residue, and is not particularly limited, as long as it is a sterol ester residue. Examples include a cholesterol ester residue, and a phytosterol ester residue. Hydrogenated products of these also may be used. Phytosterol ester residues, purely plant in origin and containing no animal-derived raw material, are more preferred.

In the formula, one of X and Y is a silicone ester residue, and is not particularly limited, as long as it is a silicone ester residue. The silicone ester residue is preferably of the following general formula (II):

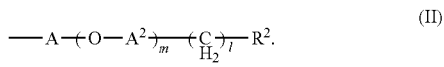
(II)

In formula (II), A and $A^2$ are each a linear or branched alkylene group of 1 to 12 carbon atoms. A is preferably a linear alkylene group, and is preferably an ethylene group or a propylene group, more preferably an ethylene group from the standpoint of excellent sensory feel. From the standpoint of excellent sensory feel, $A^2$ is preferably an ethylene group or a propylene group, more preferably an ethylene group.

The symbol m is an integer of 0 to 10, and is preferably an integer of 0 to 3, more preferably an integer of 1 or 2 from the standpoint of sensory feel. The symbol l is an integer of 0 to 2, and is preferably 1 or 2, more preferably 1 from the standpoint of sensory feel.

The silicone ester residue is represented by the following group of general formulae (III), for example.

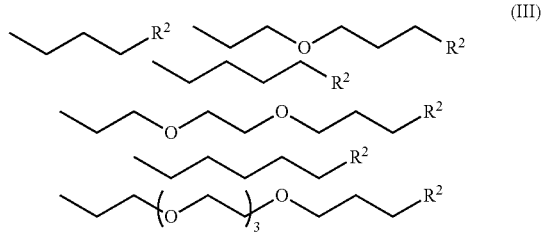
(III)

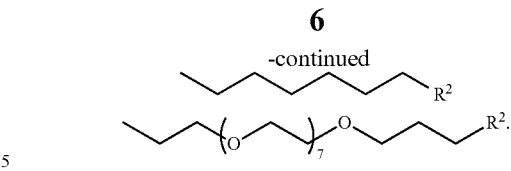

In formulae (II) and (III), $R^2$ is represented by the general formula (IV) or (V) below. From the standpoint concerning ungreasy feeling, the following general formula (IV) is preferable.

$$R^3\text{—}(\text{Si}(R^4)(R^5)\text{—O})_a\text{—Si}(R^6)(R^7)\text{—}$$
(IV)

In the formula, $R^3$, $R^4$, $R^5$, $R^6$, and $R^7$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms. From the standpoint of excellent sensory feel, $R^3$ is preferably a linear alkyl group or a phenyl group, further preferably a methyl group or a n-butyl group. In the formula, $R^4$, $R^5$, $R^6$, and $R^7$ are preferably a linear alkyl group or a phenyl group, further preferably a methyl group or a phenyl group from the standpoint of the ease of production method.

The symbol a represents a number of from 2 to 10,000, preferably 2 to 1,000, more preferably 2 to 500, even more preferably 2 to 200, further preferably 2 to 100.

$$R^8\text{—}(\text{Si}(R^9)(R^{10})\text{—O})_c\text{—}(\text{Si}(R^{11})\text{—O})_b\text{—Si}(R^{12})(R^{13})\text{—}R^{14}$$
(V)

In the formula, $R^8$, $R^9$, $R^{10}$, $R^{11}$, $R^{12}$, $R^{13}$, and $R^{14}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and is preferably an alkyl group or a phenyl group, further preferably a methyl group or a phenyl group from the standpoint of the ease of production method.

The symbol b represents a number of from 1 to 30, and is preferably 1 to 10, more preferably 1 to 5, further preferably 1 to 3 from the standpoint concerning ungreasy feeling.

The symbol c represents a number of from 1 to 10,000, and is preferably 1 to 1,000, further preferably 1 to 100 from the standpoint concerning ungreasy feeling.

A specific example of general formula (IV) is as follows.

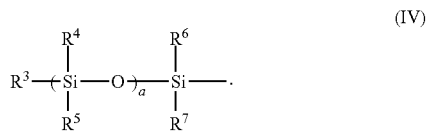
(VI)

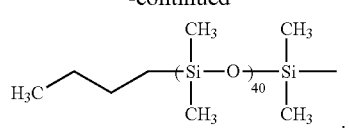
A specific example of general formula (V) is as follows.
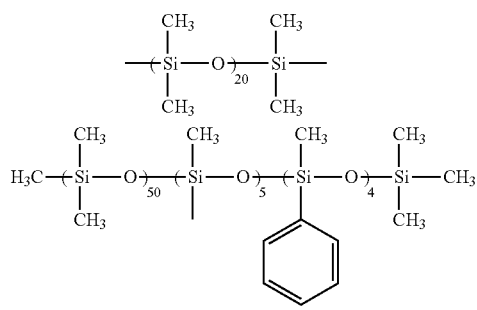
(VII)
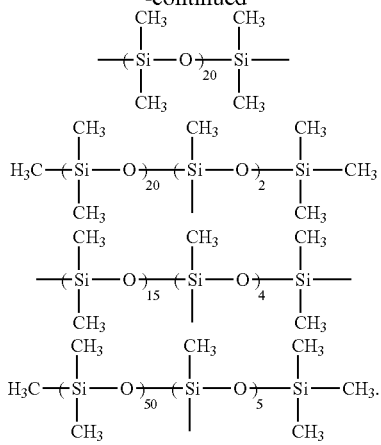
The acyl acidic amino acid monosilicone monosterol ester of the present invention can be synthesized, for example, by the reaction of equivalent amounts of acyl acidic amino acid anhydride and carbinol-modified silicone, followed by condensation with cholesterol (scheme 1).
Scheme 1.
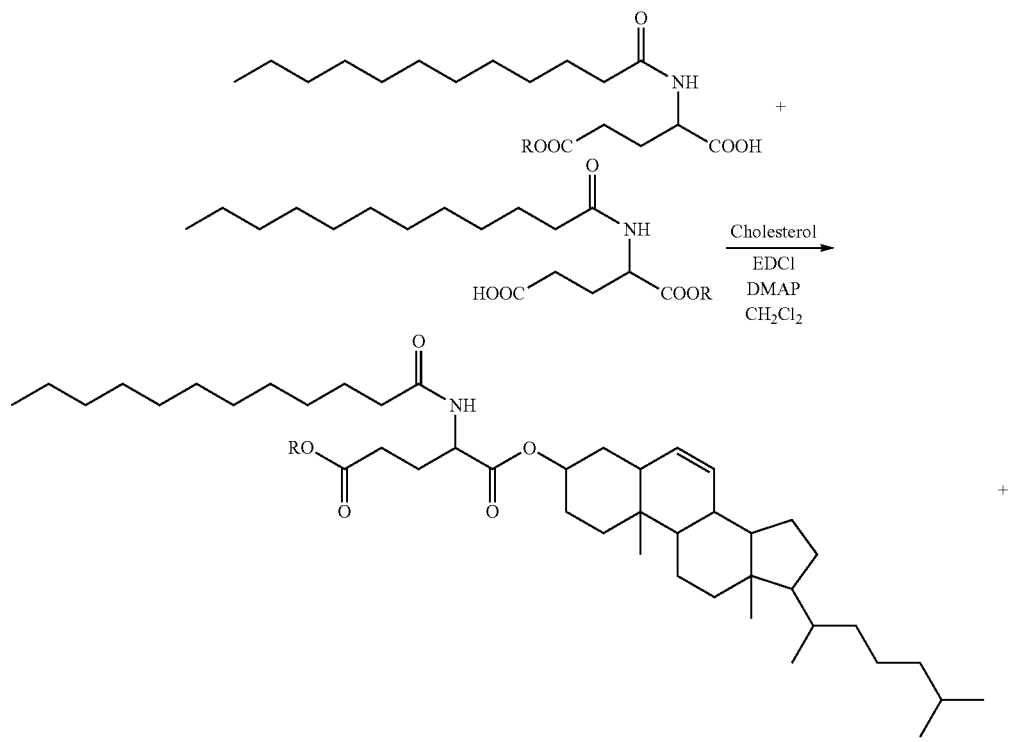

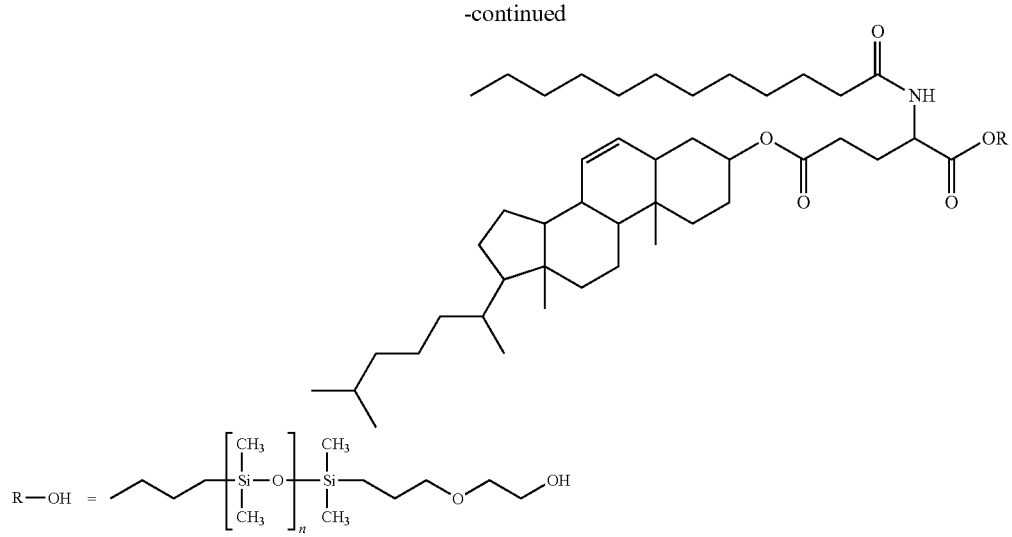
The acyl acidic amino acid monosilicone monosterol ester of the present invention also can be synthesized by the condensation reaction of allyloxy alcohol and acylglutamic acid monosterol ester, and subsequent reaction of the condensate with α-hydrogen polysiloxane (scheme 2).
Scheme 2.
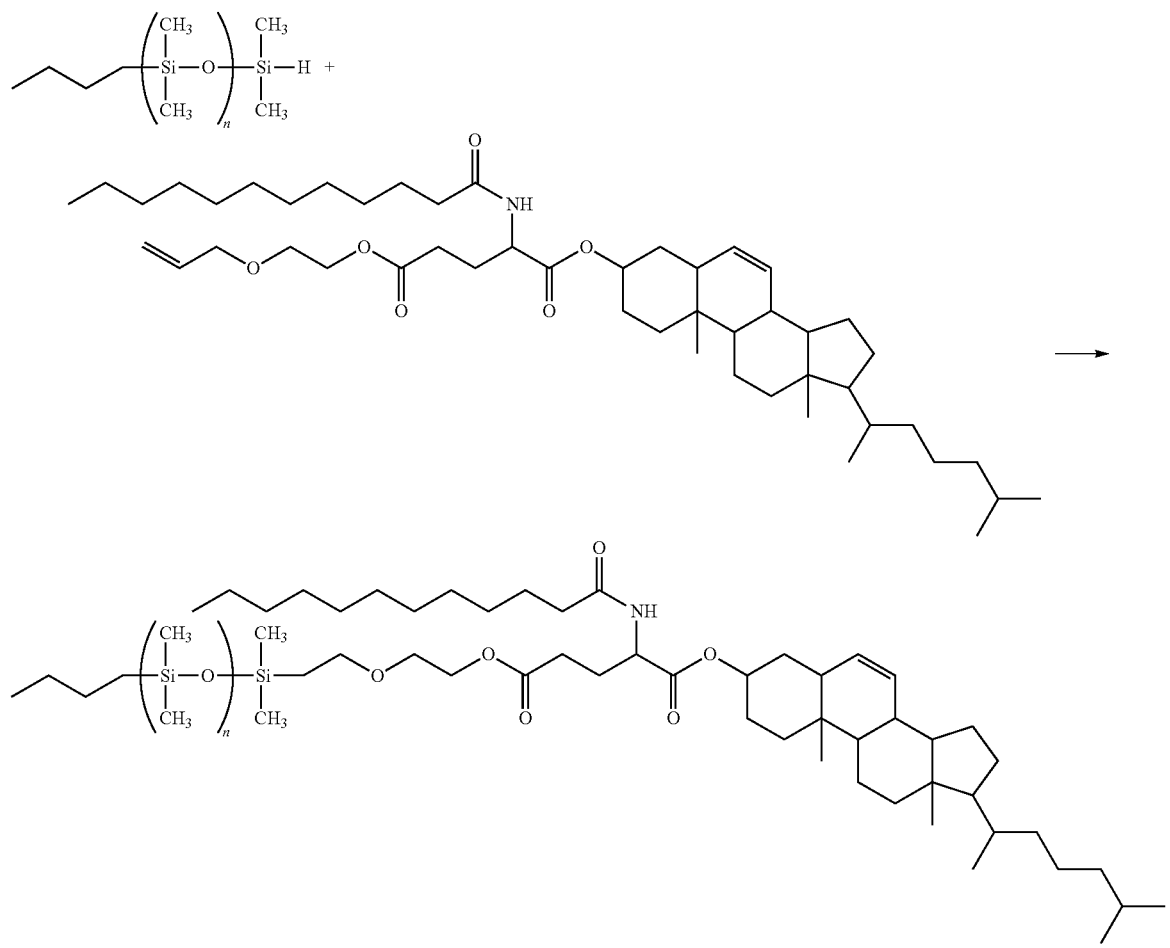

The acyl acidic amino acid monosilicone monosterol ester of the present invention can be used as an oily base. As used herein, the term oily base refers to oil-soluble components blended into cosmetics, topical agents, and the like in expectation of obtaining emollient effects, including moisture retaining effect, softening effect, protective effect, and moisture evaporation suppressing effect for skin and hair, and for obtaining other effects such as enhanced sensory feel, supplemental emulsification, consistency, dye dispersion, pigment dispersion, and spreading on skin.

The acyl acidic amino acid monosilicone monosterol ester can be used in a proportion of 0.001 to 100 mass % of the total amount of the oily base used. From the standpoint of sensory feel, the lower limit of the acyl acidic amino acid monosilicone monosterol ester content in the total amount of the oily base is preferably 0.1 mass %, more preferably 0.5 mass %, further preferably 1 mass %, even more preferably 2 mass %, yet more preferably 3 mass %, and particularly preferably 5 mass %. From the standpoint of sensory feel, the upper limit of the acyl acidic amino acid monosilicone monosterol ester content in the total amount of the oily base is preferably 98 mass %, more preferably 95 mass %, particularly preferably 90 mass %.

Ungreasy and unsticky feeling can be imparted when the oily base of the present invention further contains an acyl acidic amino acid disilicone ester.

In the present invention, the acyl acidic amino acid disilicone ester is represented by the following general formula (VIII):

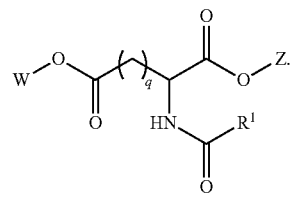

In the formula, $R^1$ and q are as defined above, Z and W are each independently a silicone ester residue, and are preferably represented by the following general formula (IX):

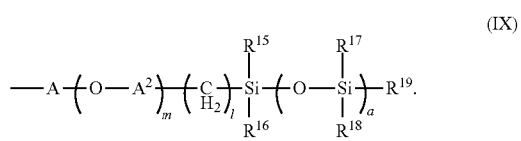

In the formula, A, $A^2$, l, m, and a are as defined above, and $R^{15}$, $R^{16}$, $R^{17}$, $R^{18}$, and $R^{19}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and are preferably linear alkyl groups or phenyl groups, more preferably methyl groups, ethyl groups, propyl groups, n-propyl groups, n-butyl groups, or phenyl groups, further preferably methyl groups, ethyl groups, or phenyl groups, even more preferably methyl groups or phenyl groups from the standpoint of excellent sensory feel. $R^{19}$ is preferably a linear alkyl group or a phenyl group, more preferably a methyl group, an ethyl group, a n-propyl group, or a n-butyl group from the standpoint of excellent sensory feel.

An example of formula (IX) is given as follows by (X):

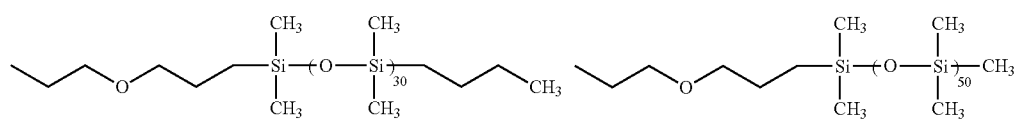

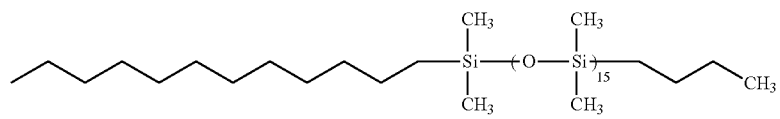

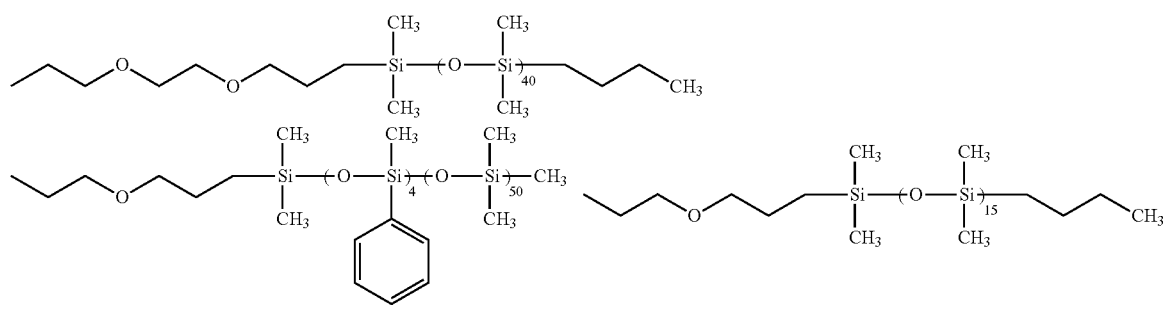

The acyl acidic amino acid disilicone ester of the present invention can be synthesized, for example, by the reaction of acyl acidic amino acid anhydride with carbinol-modified silicone, followed by further reaction with the carbinol-modified silicone using a condensing agent such as carbodiimide (scheme 3).

The acyl acidic amino acid disilicone ester also can be synthesized from the condensate of α-hydrogen polysiloxane, allyloxy alcohol, and acylglutamic acid sterol ester (scheme 4).

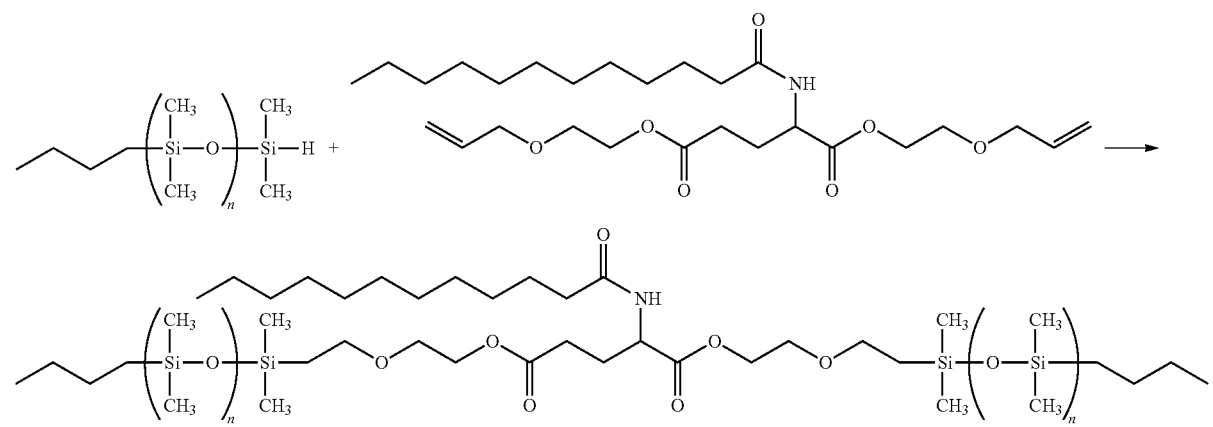

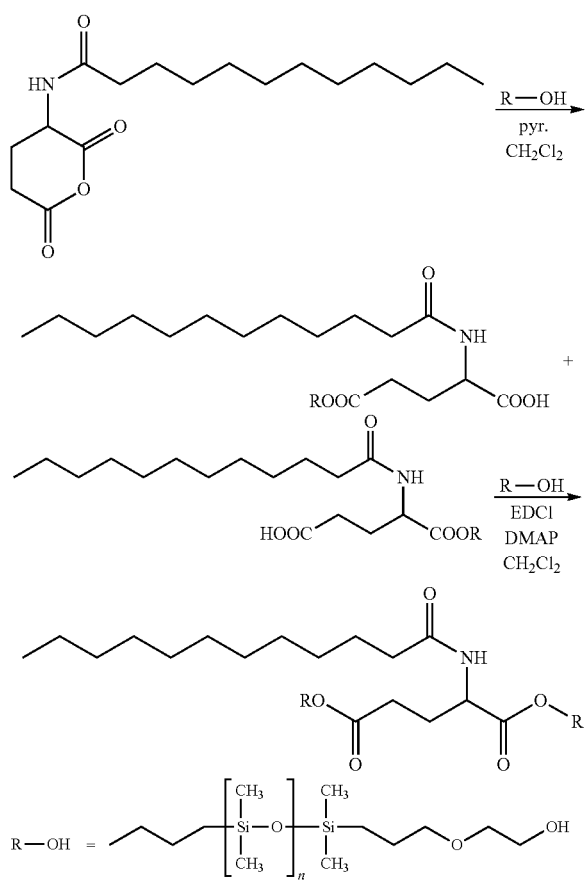

From the standpoint of effectively obtaining the actual experience of unsticky and moisturized feeling, the mixed amount of the acyl acidic amino acid monosilicone monosterol ester (hereinafter, also referred to as "component A") and the acyl acidic amino acid disilicone ester (hereinafter, also referred to as "component B") in the oily base of the present invention is such that the lower limit of component B/component A (mass ratio) is preferably 0.0001, more preferably 0.001, further preferably 0.01, even more preferably 0.1, yet more preferably 0.2, and particularly preferably 0.3. On the other hand, from the standpoint of effective obtaining affinity for skin, the upper limit of component B/component A (mass ratio) is preferably 10,000, more preferably 1,000, further preferably 100, even more preferably 10, yet more preferably 5, particularly preferably 3.

In an aspect of the present invention, a process for producing a composition that contains the acyl acidic amino acid monosilicone monosterol ester is provided, whereby acyl acidic amino acid, carbinol-modified silicone, and sterol are mixed, and esterified under an acidic catalyst.

Examples of usable acyl acidic amino acid include lauroylglutamic acid, stearoylglutamic acid, cocoylglutamic acid, and lauroylaspartic acid. Amisoft LA-D (Ajinomoto Co., Inc.) is an example of the commercially available products of such materials. The acyl acidic amino acid may be used in the form of a salt, such as a sodium salt and a potassium salt, or in the form of an anhydride. The N-acylamino acid may be either an optically active compound or a racemate.

As used herein, the carbinol-modified silicone refers to compounds with a part of the silicone chain modified by, for example, an alkyl chain that has a hydroxyl group. Examples of usable carbinol-modified silicone include FM-0411 (Chisso), FM-0421 (Chisso), X-22-4039 (Shin-Etsu Chemical Co., Ltd.), X-22-4015 (Shin-Etsu Chemical Co., Ltd.), X-22-170BX (Shin-Etsu Chemical Co., Ltd.), and X-22-170DX (Shin-Etsu Chemical Co., Ltd.), which are all commercially available. Examples of usable sterols include cholesterol and phytosterol. Examples of the commercially available products of such material include phytosterol S (Tama Biochemical Co., Ltd.), Nikkol Nikkomulese LC (Nikko Chemicals Co., Ltd.), and Cholesterol (Nippon Fine Chemical).

The amounts of acyl acidic amino acid, carbinol-modified silicone, and sterol used are selected from the ranges of x=0.01 to 1 and y=0.3 to 2, where x and y represent the equivalents of the sterol and mono-terminal carbinol-modified silicone for 1 equivalent of the acyl acidic amino acid. From the standpoint of realizing both moisturized and unsticky feeling, the lower limit of x is preferably 0.03, more preferably 0.05, further preferably 0.1. From the standpoint of providing a good balance between moisturized and unsticky feeling, the upper limit of x is preferably 0.9, more preferably 0.8, further preferably 0.7, even more preferably 0.6.

From the standpoint of enhancing the ungreasy feeling, the lower limit of y is preferably 0.5, more preferably 1.0, further preferably 1.2, even more preferably 1.4, yet more preferably 1.5. From the standpoint of obtaining a reasonable level of ungreasy feeling, the upper limit of y is preferably 1.9, more preferably 1.8, further preferably 1.7, even more preferably 1.6.

The acidic catalyst is not particularly limited, as long as it promotes esterification. Specific examples include hydrochloric acid, sulfuric acid, phosphoric acid, p-toluenesulfonic acid, and methanesulfonic acid. From the standpoint of less coloring and lower cost, hydrochloric acid, sulfuric acid, and p-toluenesulfonic acid are preferable, and p-toluenesulfonic acid, and sulfuric acid are more preferable. The amount of catalyst used is not particularly limited, as long as it promotes esterification. The lower limit is preferably 0.0001 equivalent, more preferably 0.0003, further preferably 0.001, particularly preferably 0.003, with respect to 1 equivalent of the acyl acidic amino acid.

Further, from the standpoint of the ease of post-processes, the upper limit is preferably 1 equivalent, more preferably 0.3, further preferably 0.1, particularly preferably 0.05.

From the standpoint of forming an azeotrope with water, the reaction solvent is preferably toluene, xylene, and the like. Further, from the standpoint of the ease of processes after the reaction, the reaction may be solvent-free.

Reaction temperature may be appropriately set according to reaction conditions. In the absence of pressure control, the reaction temperature is preferably 180 to 80° C., more preferably 170 to 105° C., further preferably 160 to 110° C. Appropriate temperatures can be set for experiments conducted under controlled pressure, such as under reduced pressure.

Reaction time may be appropriately set according to the scale of reaction. For example, a reaction time of 0.1 to 100 hours may be set. The reaction time is more preferably 0.5 to 60 hours, further preferably 1 to 20 hours. The reaction may be finished in 2 to 5 hours.

The composition of the present invention can be obtained by neutralizing the reaction product with a basic compound such as sodium hydroxide, followed by layer separation by addition of water, methanol, or the like, and the subsequent removal of water and the methanol phase.

The resulting composition contains the acyl acidic amino acid monosilicone monosterol ester, and may be obtained as a single component by using a known purification method, or may be directly used as an oily base. From the standpoint of obtaining good sensory feel, the composition is preferably used directly as an oily base.

A composition that imparts a further improved moisturized feeling can be obtained with a higher alcohol additionally used in the esterification reaction during the preparation of the composition of the present invention. The higher alcohol that can be used in the reaction is not particularly limited, and is preferably a linear or branched, saturated or unsaturated alkanol of 8 to 30 carbon atoms, such as cetyl alcohol, isostearyl alcohol, lauryl alcohol, hexadecyl alcohol, octyldodecanol, and behenyl alcohol, further preferably hexadecyl alcohol, and octyldodecanol.

The amounts of acyl acidic amino acid, carbinol-modified silicone, sterol, and higher alcohol used are selected from the ranges of x=0.01 to 1.2, y=0.3 to 2, and z=0.1 to 1.7, where x, y, and z are the equivalents of the sterol, mono-terminal carbinol-modified silicone, and higher alcohol, respectively, with respect to 1 equivalent of the acyl acidic amino acid.

From the standpoint of realizing both moisturized and unsticky feeling, the lower limit of x is preferably 0.03, more preferably 0.05, further preferably 0.1, even more preferably 0.2, yet more preferably 0.3. From the standpoint of realizing a good balance between moisturized and unsticky feeling, the upper limit of x is preferably 1.1, more preferably 1.0, further preferably 0.9, even more preferably 0.7.

From the standpoint of enhancing ungreasy feeling, the lower limit of y is preferably 0.5, more preferably 0.6, further preferably 0.7, even more preferably 0.8, yet more preferably 0.9. From the standpoint of obtaining a reasonable level of ungreasy feeling, the upper limit of y is preferably 1.9, more preferably 1.8, further preferably 1.7, even more preferably 1.6, yet more preferably 1.5.

From the standpoint of enhancing moisturized feeling, the lower limit of z is preferably 0.2, more preferably 0.3, further preferably 0.4, even more preferably 0.5. From the standpoint of obtaining a reasonable level of ungreasy feeling, the upper limit of z is preferably 1.4, more preferably 1.1, further preferably 1.0, even more preferably 0.9, yet more preferably 0.8, particularly preferably 0.7.

The resulting composition contains the acyl acidic amino acid monosilicone monosterol ester, and may be obtained as a single component by using a known purification method, or may be directly used as an oily base. From the standpoint of obtaining good sensory feel, the composition is preferably used directly as an oily base.

From the standpoint concerning ungreasy, sticky and moisturized feeling, and the spread of the oil solution, the composition preferably has a viscosity of 10 to 700 mPa·s. The viscosity is more preferably 40 to 600 mPa·s, further preferably 50 to 500 mPa·s. The viscosity can be adjusted by appropriately selecting silicone. From this standpoint, a in (IV) and (IX) is preferably 2 to 1,000, more preferably 2 to 500, further preferably 2 to 200, even more preferably 2 to 100. The viscosity also can be adjusted by appropriately selecting x, y, and z. From this standpoint, the lower limit of x is preferably 0.03, more preferably 0.05, further preferably 0.1. The upper limit is preferably 0.9, more preferably 0.8, further preferably 0.7, even more preferably 0.6. The lower limit of y is preferably 0.5, more preferably 1.0, further preferably 1.2, even more preferably 1.4, yet more preferably 1.5. The upper limit is preferably 1.9, more preferably 1.8, further preferably 1.7, even more preferably 1.6.

In an aspect of the present invention, cosmetics are provided that include the acyl acidic amino acid monosilicone monosterol ester. Examples of the cosmetics include skin care cosmetics such as face washes, lotions, emulsions, creams, gels, cosmetic sera, masks, and mask sheets; make-up cosmetics such as white face powder, foundations, lipsticks, cheek colors, eyeliners, mascaras, eyeshadows, and pencils;

and hair-care cosmetics such as shampoos, rinses, hair conditioners, hair styling agents, and hair treatments. The amount of the acyl acidic amino acid monosilicone monosterol ester used in the cosmetics may be appropriately selected according to intended use. For example, in lipsticks, the acyl acidic amino acid monosilicone monosterol ester may be used in an amount of 0.01 to 20 mass % with respect to the total mass of the cosmetic. In cream cosmetics, the acyl acidic amino acid monosilicone monosterol ester may be used in an amount of 0.01 to 5 mass % with respect to the total mass of the cosmetic.

The cosmetics of the present invention may include components added to common cosmetics, to the extent that such addition does not inhibit the effects of the present invention. Specific examples of such components include oil solutions, chelating agents, surfactants, powders, amino acids, polyalcohols, polyamino acids and salts thereof, water-soluble polymers, sugar alcohols and alkylene oxide adducts thereof, lower alcohols, animal and plant extracts, nucleic acids, vitamins, enzymes, anti-inflammatory agents, disinfectants, antiseptics, antioxidizing agents, ultraviolet absorbers, antiperspirants, pigments, dyes, oxidative dyes, organic and inorganic powders, pH adjusters, pearling agents, and wetting agents.

Examples of the oil solution include higher alcohols such as cetyl alcohol, isostearyl alcohol, lauryl alcohol, hexadecyl alcohol, and octyldodecanol; fatty acids such as isostearic acid, undecylenic acid, and oleic acid; polyalcohols such as glycerine, sorbitol, ethylene glycol, propylene glycol, and polyethylene glycol; esters such as myristyl myristate, hexyl laurate, decyl oleate, isopropyl myristate, hexyldecyl dimethyl octanoate, glycerine monostearate, diethyl phthalate, ethylene glycol monostearate, octyl oxystearate, and benzoic acid alkyl ester; hydrocarbons such as liquid paraffin, polyisobutene, vaseline, and squalane; waxes such as lanolin, reduced lanolin, and carnauba wax; oils and fats such as mink oil, cacao oil, coconut oil, palm kernel oil, camellia oil, sesame oil, castor oil, and olive oil; and cooligomers of ethylene and α-olefin.

Examples of the silicone oil include silicon oils selected from the group consisting of methylpolysiloxane, polymeric methylpolysiloxane, ether-modified silicones (such as polyoxyethylene•methylpolysiloxane copolymers, polyoxypropylene•methylpolysiloxane copolymers, and poly(oxyethylene, oxypropylene)•methylpolysiloxane copolymers), stearoxymethylpolysiloxane, stearoxytrimethylsilane, methylhydrogen polysiloxane, cyclic silicones (such as decamethylcyclopentasiloxane, octamethylcyclotetrasiloxane, tetrahydrotetramethylcyclotetrasiloxane, methylcyclopolysiloxane, and dodecamethylcyclohexasiloxane), methylphenylpolysiloxane, trimethylsiloxysilicate, amino-modified silicones (such as aminoethylaminopropylsiloxane•dimethylsiloxane copolymers), silanol-modified polysiloxane, alkoxy-modified polysiloxane, fatty acid-modified polysiloxane, fluorine-modified polysiloxane, epoxy-modified polysiloxane, alkoxy-modified polysiloxaneperfluoropolyether, polyvinyl acetate dimethyl polysiloxane, and mixtures thereof.

The chelating agent is not particularly limited. Preferred examples include chelating agents selected from the group consisting of triethylenetetramine, 2-thenoyltrifluoroacetone, thioglycolic acid, tartaric acid, succinic acid, 8-quinolinol, pyridine-2,6-dicarboxylic acid, pyridine, 1,10-tenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone, and salts thereof, and mixtures of these.

Examples of the surfactant include:

anionic surfactants, including N-long-chain acylamino acid salts (such as N-long-chain acyl acidic amino acid salts and N-long-chain acyl neutral amino acid salts), N-long-chain fatty acid acyl-N-methyl taurates, alkyl sulfates and alkylene oxide adducts thereof, fatty acid amide ether sulfates, metal salts and weak base salts of fatty acids, sulfosuccinate surfactants, alkylphosphates and alkylene oxide adducts thereof, and alkyl ether carboxylic acids;

nonionic surfactants, including ether-type surfactants (such as glycerine ether and alkylene oxide adducts thereof), ester-type surfactants (such as glycerine ester and alkylene oxide adducts thereof), ether ester-type surfactants (such as sorbitan esters and alkylene oxide adducts thereof), ester-type surfactants (such as polyoxyalkylene fatty acid ester, glycerine ester, fatty acid polyglycerine ester, sorbitan ester, and sucrose fatty acid ester), alkylglucosides, hydrogenated castor oil pyroglutamic acid diesters and ethylene oxide adducts thereof, and nitrogen-containing nonionic surfactants (such as fatty acid alkanolamides);

cationic surfactants, including aliphatic amine salts (such as alkylammonium chloride, and dialkylammonium chloride), quaternary ammonium salts thereof, aromatic quaternary ammonium salts (such as benzalkonium salt), and fatty acid acyl arginine esters; and ampholytic surfactants, including betaine-type surfactants (such as carboxybetaine), aminocarboxylic acid-type surfactants, and imidazoline-type surfactants.

Examples of the powder include resin powders (such as nylon beads, and silicone beads), nylon powder, metal fatty acid soap, yellow iron oxide, red iron oxide, black iron oxide, chromium oxide, cobalt oxide, carbon black, ultramarine, iron blue, zinc oxide, titanium oxide, zirconium oxide, silicon oxide, aluminum oxide, cerium oxide, titanated mica, boron nitride, barium sulfate, calcium carbonate, magnesium carbonate, aluminum silicate, magnesium silicate, silicon carbide, dye, lake, sericite, mica, talc, kaolin, plate-shaped barium sulfate, butterfly-shaped barium sulfate, fine particles of titanium oxide, fine particles of zinc oxide, fine particles of iron oxide, and acyl amino acids (such as acyl lysine, acyl-glutamic acid, acylarginine, and acylglycine). These may be additionally subjected to surface treatments such as silicone treatment, fluorine compound treatment, silane coupling agent treatment, silane treatment, organic titanate treatment, acylated lysine treatment, fatty acid treatment, metallic soap treatment, oil solution treatment, and amino acid treatment.

Examples of the amino acid include glycine, alanine, serine, threonine, arginine, glutamic acid, aspartic acid, isoleucine, leucine, and valine.

Examples of the polyalcohol include glycerine, ethylene glycol, 1,3-butylene glycol, propylene glycol, and isoprene glycol.

Examples of the polyamino acid and salts thereof include polyglutamic acid, and polyaspartic acid.

Examples of the water-soluble polymer include polyethylene glycol, gum arabic, alginate, xanthan gum, hyaluronan, hyaluronate, chitin, chitosan, water-soluble chitin, carboxyvinyl polymer, carboxymethyl cellulose, hydroxyethyl cellulose, hydroxypropyltrimethylammonium chloride, poly (dimethylmethylene piperidium chloride), quaternary ammoniums of polyvinylpyrrolidone derivatives, cationized proteins, collagen decomposition products and derivatives thereof, acylated proteins, and polyglycerine.

Examples of the sugar alcohol and alkylene oxide adducts thereof include mannitol.

Examples of the lower alcohol include ethanol, and propanol.

Other features of the invention will become apparent in the course of the following descriptions of exemplary embodiments which are given for illustration of the invention and are not intended to be limiting thereof.

EXAMPLES

Raw Materials Used

Mono-terminal carbinol-modified silicone: FM-0411 (Chisso, average molecular weight: 1,120)

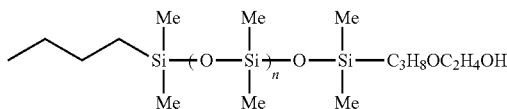

Lauroylglutamic acid: Amisoft LA-D (Ajinomoto Co., Inc.)
Cholesterol: Cholesterol (Wako Pure Chemical Industries, Ltd.)
Phytosterol: Phytosterol S (Tama Biochemical Co., Ltd., molecular weight was calculated as 414.7)
Measurements.

AVANCE 400 (Bruker) was used for $^1$H-NMR measurement.

Viscosity was measured using AR-G2 (TA-Instruments). Geometry was measured using an aluminum cone plate ($\phi$, 40 mm) under steady state flow conditions; the value at the shear stress of 9 Pa was used.

Acid number was measured according to the method of the Japanese Standards of Quasi-Drug Ingredients 2006.

Hydroxyl number was measured according to JIS standard (JIS K0070, Test Methods for Acid Value, Saponification Value, Ester Value, Iodine Value, Hydroxyl Value, and Unsaponifiable Matter of Chemical Produces).

Reaction rate was calculated by comparing the hydroxyl number of the product with the theoretical hydroxyl number before reaction.

Specifically, (reaction rate)=(1−(hydroxyl number of product)/(theoretical hydroxyl number before reaction))×100(%)

Example 1

Synthesis of Lauroylglutamic Acid Monosilicone Monocholesterol Ester 10.00 g (0.00892 mol) of mono-terminal carbinol-modified silicone was dissolved in 10.00 g of methylene chloride and 1.00 g of pyridine. 4.67 g (0.0150 mol) of lauroylglutamic acid anhydride was added to the reaction mixture, and then the mixture was stirred overnight. The reaction liquid was concentrated and separated after adding hexane and a 90% methanol aqueous solution. The hexane layer was concentrated to obtain 10.64 g (0.00753 mol) of lauroylglutamic acid-modified silicone.

2.00 g (0.00141 mol) of the product and 0.649 g (0.00168 mol) of cholesterol were dissolved in 5.00 g of methylene chloride, and 0.439 g (0.00229 mol) of (1-ethyl-(3-dimethylamino)propyl)carbodiimide hydrochloride (EDCI) and 0.037 g of 4-dimethylaminopyridine (DMAP) were added to the reaction mixture, and then the mixture was stirred overnight. The reaction liquid was concentrated and separated after adding hexane and a 90% methanol aqueous solution. The hexane layer was concentrated and purified by silica gel column chromatography (hexane/ethyl acetate=10/1 and 4/1) to obtain 1.37 g (00.00815 mol) of lauroylglutamic acid monosilicone monocholesterol ester.

$^1$H-NMR (400 MHz, CDCl$_3$, r.t.): δ 6.13 (1H, d, J=7.6 Hz), 5.29 (1H, s), 4.60-4.48 (2H, m), 4.21 (2H, m), 3.55 (2H, t, J=4.9 Hz), 3.34 (2H, t, J=4.9 Hz), 2.4-0.8 (75H, m), 0.60 (3H, s), 0.45 (4H, m), 0.05 to −0.05 (about 80H, m)

Example 2

Synthesis of Lauroylglutamic Acid Disilicone Ester 10.00 g (0.00708 mol) of lauroylglutamic acid-modified silicone synthesized as in Example 1, and 3.81 g (0.00340 mol) of mono-terminal carbinol-modified silicone were dissolved in 40.00 g of methylene chloride. 1.46 g (0.00763 mol) of (1-ethyl-(3-dimethylamino)propyl)carbodiimide hydrochloride (EDCI), and 0.093 g of 4-dimethylaminopyridine (DMAP) were added to the reaction mixture, and then the mixture was stirred overnight. The reaction liquid was concentrated and separated after adding hexane and a 90% methanol aqueous solution. The hexane layer was concentrated and purified by silica gel column chromatography (hexane/ethyl acetate=10/1 and 4/1) to obtain 8.49 g (0.00338 mol) of lauroylglutamic acid disilicone ester.

$^1$H-NMR (400 MHz, CDCl$_3$, r.t.): δ 6.14 (1H, d, J=7.8 Hz), 4.58 (1H, dt, J=4.9, 7.8 Hz), 4.30-4.08 (4H, m), 3.55 (4H, m), 3.34 (2H, m), 2.52-1.90 (6H, m), 1.54 (6H, m), 1.21 (24H, m), 0.81 (9H, m), 0.46 (8H, m), 0.05 to −0.05 (about 160H, m)

Production Example 1

Preparation of Lauroylglutamic Acid Monosilicone Monocholesterol Ester and Lauroylglutamic Acid Disilicone Ester Composition 9.88 g (0.0300 mol) of lauroylglutamic acid, 3.48 g (0.0090 mol) of cholesterol, 51.00 g (0.0455 mol) of mono-terminal-modified silicone, and 71.85 g of toluene were mixed and heat-dissolved. After adding 0.3 g of sulfuric acid, reaction was performed using a Dean-Stark at 130° C. for 4 hours. 20 g of water was added after the reaction, and the solution was neutralized to pH 7 with 10% NaOH aqueous solution. The liquid was then separated with addition of hexane (20 g), ethyl acetate (40 g), and methanol (20 g), and the aqueous layer was removed. The liquid was further separated with addition of water (20 g), methanol (30 g), ethyl acetate (30 g), and hexane (30 g), and the aqueous layer was removed. The organic layer was concentrated to obtain an oil (53.45 g). The acid number of the oil was 1.01. The hydroxyl number was 7.50, the reaction rate 84%, and the product viscosity 113.8 mPa·s.

Production Example 2

Preparation of Lauroylglutamic Acid Di(Cholesteryl/Hexyldecyl/Polydimethylsiloxane). Here and below, the slash used in the composition name means "and/or."

9.88 g (0.0300 mol) of lauroylglutamic acid, 3.48 g (0.0090 mol) of cholesterol, 30.00 g (0.0268 mol) of mono-terminal-modified silicone, 5.09 g (0.0188 mol) of hexyldecanol, and 60.00 g of toluene were mixed and heat-dissolved. After adding 0.3 g of sulfuric acid, reaction was performed using a Dean-Stark at 130 degrees for 4 hours. 20 g of water was added after the reaction, and the solution was neutralized to pH 7 with 10% NaOH aqueous solution. The liquid was then separated with addition of hexane (20 g), ethyl acetate (40 g), and methanol (20 g), and the aqueous layer was removed. The liquid was further separated with addition of water (20 g), methanol (60 g), ethyl acetate (60 g), and hexane (20 g), and the aqueous layer was removed. The organic layer was concentrated to obtain oil (41.84 g). The acid number of the oil was 1.57. The hydroxyl number was 9.44, the reaction rate 85%, and the product viscosity 127.5 mPa·s.

Production Example 3

Preparation of Lauroylglutamic Acid Di (Phytosteryl/Octyldodecyl/Polydimethylsiloxane)

24.71 g (0.075 mol) of lauroylglutamic acid, 8.70 g (0.021 mol) of phytosterol, 84.00 g (0.075 mol) of mono-terminal-modified silicone, 14.94 g (0.0525 mol) of octyldodecanol, and 105.00 g of toluene were mixed and heat-dissolved. After adding 1.43 g of p-toluenesulfonic acid, reaction was performed using a Dean-Stark at 130 degrees for 2 hours. 80 g of water was added after the reaction, and the solution was neutralized to pH 7 with 10% NaOH aqueous solution. The liquid was then separated with addition of hexane (240 g) and methanol (240 g), and the aqueous layer was removed. The liquid was further separated with addition of methanol (240 g) and water (24 g), and the aqueous layer was removed. The organic layer was concentrated to obtain oil (109.32 g). The acid number of the oil was 3.87. The hydroxyl number was 15.20, the reaction rate 76%, and the product viscosity 110.5 mPa·s.

Production Example 4

Preparation of Lauroylglutamic Acid Di (Phytosteryl/Octyldodecyl/Polydimethylsiloxane)

9.88 g (0.0300 mol) of lauroylglutamic acid, 4.18 g (0.0108 mol) of phytosterol, 40.32 g (0.0360 mol) of mono-terminal-modified silicone, 4.27 g (0.0150 mol) of octyldodecanol, and 70.00 g of toluene were mixed and heat-dissolved. After adding 0.57 g of p-toluenesulfonic acid, reaction was performed using a Dean-Stark at 130 degrees for 2 hours. After the reaction, the liquid was separated with addition of 2% NaOH aqueous solution (60 g), hexane (60 g), and methanol (60 g), and the aqueous layer was removed. The liquid was further separated with addition of methanol (60 g) and water (6 g), and the aqueous layer was removed. This procedure was repeated twice. The organic layer was concentrated to obtain an oil (49.23 g). The acid number of the oil was 1.1. The hydroxyl number was 10.69, the reaction rate 82%, and the product viscosity 103.1 mPa·s.

Production Example 5

Preparation of Lauroylglutamic Acid Di (Phytosteryl/Octyldodecyl/Polydimethylsiloxane)

9.88 g (0.0300 mol) of lauroylglutamic acid, 2.78 g (0.0067 mol) of phytosterol, 26.88 g (0.0240 mol) of mono-terminal-modified silicone, 7.68 g (0.0270 mol) of octyldodecanol, and 70.00 g of toluene were mixed and heat-dissolved. After adding 0.57 g of p-toluenesulfonic acid, reaction and post-processes were performed according to the method of Production Example 4 to obtain an oil (38.69 g). The acid number of the oil was 0.9. The hydroxyl number was 14.7, the reaction rate 79%, and the product viscosity 113.1 mPa·s.

Production Example 6

Preparation of Lauroylglutamic Acid Di (Phytosteryl/Octyldodecyl/Polydimethylsiloxane)

9.88 g (0.0300 mol) of lauroylglutamic acid, 1.74 g (0.0042 mol) of phytosterol, 16.80 g (0.0150 mol) of mono-terminal-modified silicone, 10.24 g (0.0360 mol) of octyldodecanol, and 90.00 g of toluene were mixed and heat-dissolved. After adding 0.57 g of p-toluenesulfonic acid, reaction and post-processes were performed according to the method of Production Example 4 to an obtain oil (29.29 g). The acid number of the oil was 0.9. The hydroxyl number was 14.9, the reaction rate 81%, and the product viscosity 111.1 mPa·s.

Production Example 7

Preparation of Lauroylglutamic Acid Di (Phytosteryl/Octyldodecyl/Polydimethylsiloxane)

9.88 g (0.0300 mol) of lauroylglutamic acid, 6.96 g (0.0168 mol) of phytosterol, 33.60 g (0.0300 mol) of mono-terminal-modified silicone, 3.41 g (0.0120 mol) of octyldodecanol, and 90.00 g of toluene were mixed and heat-dissolved. After adding 0.57 g of p-toluenesulfonic acid, reaction and post-processes were performed according to the method of Production Example 4 to obtain an oil (41.87 g). The acid number of the oil was 1.4. The hydroxyl number was 20.0, the reaction rate 67%, and the product viscosity 135.8 mPa·s.

Production Example 8

Preparation of Lauroylglutamic Acid Di (Phytosteryl/Polydimethylsiloxane)

9.88 g (0.0300 mol) of lauroylglutamic acid, 3.48 g (0.0084 mol) of phytosterol, 57.12 g (0.0510 mol) of mono-terminal-modified silicone, and 90.00 g of toluene were mixed and heat-dissolved. After adding 0.57 g of p-toluenesulfonic acid, reaction and post-processes were performed according to the method of Production Example 4 to obtain an oil (57.94 g). The acid number of the oil was 0.8. The hydroxyl number was 14.0, the reaction rate 70%, and the product viscosity 61.6 mPa·s.

Production Example 9

Preparation of Lauroylglutamic Acid Di (Phytosteryl/Polydimethylsiloxane)

9.88 g (0.0300 mol) of lauroylglutamic acid, 5.80 g (0.0140 mol) of phytosterol, 16.80 g (0.0150 mol) of mono-terminal-modified silicone, and 90.00 g of toluene were mixed and heat-dissolved. After adding 0.57 g of p-toluenesulfonic acid, reaction and post-processes were performed according to the method of Production Example 4 to obtain an oil (31.65 g). The acid number of the oil was 0.8. The hydroxyl number was 16.8, the reaction rate 80%, and the product viscosity 247.8 mPa·s.

Sensory Evaluations of Oil Solutions of Examples 3 to 17.

Sensory evaluations were performed for the oil solutions produced as above. The results are presented in Table 1.

Testing in sensory evaluation was performed by a panel of five experts. Specifically, each sample was applied in an appropriate amount to the back of the hand of each tester, and evaluated according to the following evaluation criteria.

greasy feeling after application (evaluated in a scale of 1 to 5)
Evaluation
- 5: not greasy at all
- 4: not greasy
- 3: Moderate
- 2: greasy
- 1: Very greasy stickiness feeling (evaluated in a scale of 1 to 5)
Evaluation
- 5: not sticky at all
- 4: not sticky
- 3: Moderate
- 2: Sticky
- 1: Very sticky Moisturized feeling after application (evaluated in a scale of 1 to 5)
Evaluation
- 5: Very moisturized feel
- 4: moisturized feel
- 3: Moderate
- 2: no moisturized feel
- 1: no moisturized feel at all Spread upon application (evaluated in a scale of 1 to 5)
Evaluation
- 5: Very easy to spread
- 4: Easy to spread
- 3: Moderate
- 2: Difficult to spread
- 1: Very difficult to spread Friction feeling upon application (evaluated in a scale of 1 to 5)
Evaluation
- 5: no friction feeling at all
- 4: no friction feeling
- 3: Moderate
- 2: friction feeling
- 1: strong friction feeling Evaluation results with the average scores of 4.6 and higher were regarded as Excellent; 3.5 to 4.5, Good; 3.0 to 3.4, Acceptable; 2.5 to 2.9, Marginally Acceptable; and 2.4 and lower, Poor. The results are presented in Table 1.

TABLE 1

|  |  | Sensory Evaluation | | | | | |
|---|---|---|---|---|---|---|---|
|  |  | Greasy feeling | sticky feeling | moisturized feeling | Spread | friction feeling | Viscosity (mPa·s) |
| Ex. 3 | A | Good | Good | Excellent | Good | Excellent | 484 |
| Ex. 4 | A:B = 3:1 | Excellent | Excellent | Excellent | Excellent | Excellent | — |
| Ex. 5 | A:B = 1:1 | Excellent | Excellent | Excellent | Excellent | Excellent | — |
| Ex. 6 | A:B = 1:3 | Excellent | Excellent | Excellent | Excellent | Excellent | — |
| Ex. 7 | A:B = 1:5 | Excellent | Excellent | Good | Excellent | Excellent | — |
| Ex. 8 | A:B = 1:10,000 | Excellent | Excellent | Good | Excellent | Excellent | 69 |
| Ex. 9 | Oily raw material composition of Production Example 1 | Excellent | Excellent | Good | Excellent | Excellent | 114 |
| Ex. 10 | Oily raw material composition of Production Example 2 | Excellent | Excellent | Good | Excellent | Excellent | 128 |
| Ex. 11 | Oily raw material composition of Production Example 3 | Excellent | Excellent | Good | Excellent | Excellent | 111 |
| Ex. 12 | Oily raw material composition of Production Example 4 | Excellent | Excellent | Good | Excellent | Excellent | 103 |
| Ex. 13 | Oily raw material composition of Production Example 5 | Good | Excellent | Good | Excellent | Excellent | 113 |
| Ex. 14 | Oily raw material composition of Production Example 6 | Excellent | Excellent | Good | Excellent | Excellent | 111 |
| Ex. 15 | Oily raw material composition of Production Example 7 | Excellent | Good | Excellent | Excellent | Excellent | 136 |
| Ex. 16 | Oily raw material composition of Production Example 8 | Excellent | Excellent | Good | Excellent | Excellent | 62 |
| Ex. 17 | Oily raw material composition of Production Example 9 | Good | Good | Excellent | Good | Excellent | 248 |
| Com. Ex. 1 | Sterol-modified silicone[*1] | Poor | Poor | Good | Poor | Poor | Solid form |
| Com. Ex. 2 | Lauroylglutamic acid-modified silicone[*2] | Poor | Poor | Poor | Poor | Poor | Solid form |
| Com. Ex. 3 | Lauroylglutamic acid di(phytosteryl/octyldodecyl)[*3] | Poor | Poor | Good | Poor | Excellent | 1,770 |
| Com. Ex. 4 | Lauroylglutamic acid di(cholesteryl/octyldodecyl)[*4] | Poor | Poor | Good | Poor | Excellent | 1,818 |

—: Not measured
A: Lauroylglutamic acid monosilicone monocholesterol ester of Example 1
B: Lauroylglutamic acid disilicone ester of Example 2
[*1]Reference Example of Japanese Pat. No. 3086241

TABLE 1-continued

| | Sensory Evaluation | | | | | Viscosity (mPa·s) |
|---|---|---|---|---|---|---|
| | Greasy feeling | sticky feeling | moisturized feeling | Spread | friction feeling | |

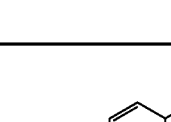

*2 Reference Example of JP-A-50-158700
*3 Eldew PS-203 (Ajinomoto Co., Inc.)
*4 Eldew CL-202 (Ajinomoto Co., Inc.)

The results revealed that the acylglutamic acid monosilicone monosterol ester spread smoothly upon application, and was moist with a ungreasy feeling and little stickiness. Friction feeling peculiar to silicone was also absent. It was also found that, as a mixture with acylglutamic acid silicone diester, the acylglutamic acid monosilicone monosterol ester could provide an oil solution that satisfies the spread, unsticky and moisturized feeling, and ungreasy feeling upon application, all at the same time.

Preparation Example 1

Preparation of Moisturizing Cream

The following W/O cream was prepared. The cream had excellent moisture retention, and good sensory feel without a friction feeling.
1. Cyclomethicone D-5 (Toray Dow Corning SH245): 20.50 g
2. Dimethicone polyol (Shin-Etsu Chemical Co., Ltd., KF-6019): 2.00 g
3. Isotridecyl isononanoate (Kokyu Alcohol Kogyo Co., Ltd., KAK-139): 5.00 g
4. Oily base composition of Production Example 3: 0.50 g
5. 1,3-Butyleneglycol: 7.00 g
6. Sodium chloride: 2.00 g
7. Water: 63.00 g
Preparation Method
Components 1 to 4 were heat-mixed, and the separately heat-mixed components 5 to 7 were added thereto. The mixture was allowed to cool while being gently stirred.

Preparation Example 2

Preparation of Lip Gloss

The following lip gloss was prepared. The lip gloss had excellent moisture retention, and good sensory feel without a friction feeling.
1. Dibutyl lauroyl glutamide (Ajinomoto Co., Inc. GP-1): 0.40 g
2. Octyldodecanol (Kokyu Alcohol Kogyo Co., Ltd., Risonol 20SP): 2.00 g
3. Triethylhexanoin (Kokyu Alcohol Kogyo Co., Ltd., TOG): 25.00 g
4. Diisostearyl malate (Nisshin OilliO Cosmol 222S): 10.00 g
5. Oily Base Composition of Production Example 4: 8.00 g
6. Tocopherol: 0.02 g
7. Hydrogenated polyisobutene (NOF Corporation, ParLeam 18): 34.48 g
8. Hydrogenated polyisobutene (NOF Corporation, ParLeam 24): 20.00 g
9. Pearl pigment: 0.10 g
Preparation Method
Components 1 and 2 were heat-mixed and dissolved, and the separately heat-dissolved components 3 to 6 were added thereto. After adding the separately heat-dissolved components 7 and 8, the mixture was allowed cool with addition of component 9.

Preparation Example 3

Preparation of Moisturizing Cream

The following W/O-type moisturizing cream was prepared. The moisturizing cream had excellent moisture retention, and good sensory feel without a friction feeling.
1. Squalane: 8.00 g
2. Cetylethylhexanoate (Kokyu Alcohol Kogyo Co., Ltd., CEH): 3.00 g
3. Cetanol (Kokyu Alcohol Kogyo Co., Ltd., Cetanol SP-D50): 2.80 g
4. Stearic acid: 2.40 g
5. Stearic acid PG (Nihon Emulsion Co., Ltd., Emalex PGMS): 1.20 g 6. Glyceryl stearate (Nikko Chemicals Co., Ltd., MGS-BSEV): 3.30 g
7. Polysorbate 60 (Kao Corporation, Rheodol TW-S120V): 0.50 g
8. Stearic acid PEG-40 (Nikko Chemicals Co., Ltd., MYS-40): 1.50 g
9. Dimethicone (Toray Dow Corning, SH200 350cs): 0.80 g
10. Oily Base Composition of Production Example 4: 1.00 g
11. BG: 5.00 g
12. Xanthan gum: 0.10 g
13. Water: 70.40 g Preparation Method Components 1 to 10 were heated and dissolved (A component). Components 11 to 13 were heat-dissolved, and gradually added to A component. The mixture was emulsified with a homomixer, and cooled to room temperature.

Preparation Example 4

Preparation of Hair Rinse

The following hair rinse was prepared. The hair rinse had good sensory feel without a friction feeling.
1. Behenamido propyl dimethylamine (Catinal BMPA, Toho Chemical Industry Co., Ltd.): 1.50 g
2. Cetearyl alcohol: 5.00 g
3. Propylene glycol: 3.50 g
4. Composition of Production Example 6: 0.50 g
5. Lauroyl arginine (Amisafe AL-01, Ajinomoto Co., Inc.): 0.30 g
6. PCA: 0.50 g
7. EDTA-2Na: 0.01 g
8. Water: 88.69 g Preparation Method Components 1 to 4 were heated to 85° C., and dissolved with stirring to prepare a dispersion with component 5 (A component). Separately, components 6 to 8 were mixed and dissolved, heated to 85° C., and gradually added to A component to emulsify. The mixture was cooled to room temperature while being gently stirred.

Preparation Example 5

Preparation of Lipstick

The following lipstick was prepared. The lipstick had excellent moisture retention, and good sensory feel without a friction feeling.
1. Polyethylene (Performalene PL polyethylene, Nikko Chemicals Co., Ltd.): 2.80 g
2. Triethylhexanoin: 15.00 g
3. Candelilla wax: 1.00 g
4. Paraffin (Paraffin 155° F., Nippon Seiro Co., Ltd.): 7.00 g
5. Microcrystalline wax: 6.00 g
6. Hydrogenated polyisobutene (ParLeam 24, NOF Corporation): 12.00 g
7. Hexa(hydroxystearic acid/stearic acid/rosin acid)dipentaerythrityl (KAK139, Kokyu Alcohol Kogyo Co., Ltd.): 5.00 g
8. Triisostearic acid trimethylolpropane: 5.00 g
9. Composition of Production Example 3: 5.00 g
10. Tocopherol: 0.10 g
11. Titanium oxide, mica, silica (Timiron Splendid Copper, Matsumoto Trading Co., Ltd.): 4.00 g
12. Mica, titanium oxide (Flamenco Sparkle Gold, MEARL): 2.00 g
13. Red 201: 0.27 g
14. Red 202: 0.54 g
15. Iron oxide: 0.70 g
16. Titanium oxide: 1.00 g
17. Polyglyceryl-2 triisostearate (Cosmol 43V, Nisshin OilliO): 22.59 g Preparation Method Components 1 and 2 were heat-dissolved at 110° C., and components 3 to 10 were added thereto, and mixed with components 11 and 12. Components 12 to 17 were further added after being dispersed with three rollers. The mixture was charged into a mold, and installed in a container after cooling.

INDUSTRIAL APPLICABILITY

The significance of the specific acyl acidic amino acid monosilicone monosterol ester of the present invention is that it can provide novel oil material and various cosmetics that spread smoothly upon application and are free from stickiness, and also give ungreasy and moisturized feeling after application, but do not give the friction feeling peculiar to silicone.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. An acyl acidic amino acid monosilicone monosterol ester of formula (I):

(I):

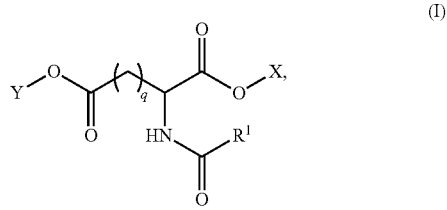

wherein $R^1$ represents a linear or branched hydrocarbon group of 1 to 30 carbon atoms, q is 1 or 2, and one of X and Y is a sterol ester residue, and the other is a silicone ester residue of formula (II):

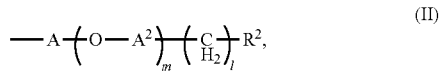

wherein A and $A^2$ are each selected from linear or branched alkylene groups of 1 to 12 carbon atoms; l is an integer of 0 to 2; m is an integer of 0 to 10, and $R^2$ is a group represented by formula (IV) or (V):

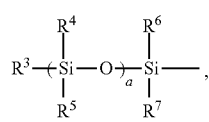

(IV)

wherein $R^3$, $R^4$, $R^5$, $R^6$, and $R^7$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and a represents a number of from 2 to 10,000;

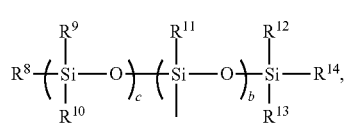

(V)

wherein $R^8$, $R^9$, $R^{10}$, $R^{11}$, $R^{12}$, $R^{13}$, and $R^{14}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, c represents a number of from 1 to 10,000, and b represents a number of from 1 to 30.

2. An acyl acidic amino acid monosilicone monosterol ester according to claim 1, wherein $R^2$ is a group represented by formula (IV).

3. An acyl acidic amino acid monosilicone monosterol ester according to claim 1, wherein q=2.

4. An acyl acidic amino acid monosilicone monosterol ester according to claim 1, wherein the acyl group represented by $R^1$—CO— is one or more selected from an octanoyl group, a 2-ethylhexanoyl group, a nonanoyl group, a decanoyl group, a lauroyl group, a myristoyl group, a palmitoyl group, a stearoyl group, and an oleoyl group.

5. An acyl acidic amino acid monosilicone monosterol ester according to claim 1, wherein the acyl group represented by $R^1$—CO— is one or more acyl groups from mixed fatty acids obtained from nature, including coconut oil fatty acid, castor oil fatty acid, olive oil fatty acid, and palm oil fatty acid, or from synthetic fatty acids (including branched fatty acids).

6. An acyl acidic amino acid monosilicone monosterol ester according to claim 1, wherein the acyl group represented by $R^1$—CO— is one or more acyl groups from coconut oil fatty acid, castor oil fatty acid, olive oil fatty acid, and palm oil fatty acid, or from synthetic fatty acids, including branched fatty acids.

7. An acyl acidic amino acid monosilicone monosterol ester according to claim 1, wherein the acyl group represented by $R^1$—CO— is a lauroyl group.

8. An acyl acidic amino acid monosilicone monosterol ester according to claim 1, wherein the acyl acidic amino acid monosilicone monosterol ester is lauroylglutamic acid monosilicone monosterol ester.

9. An acyl acidic amino acid monosilicone monosterol ester according to claim 1, wherein a is 2 to 100.

10. A cosmetic, comprising an acyl acidic amino acid monosilicone monosterol ester according to claim 1.

11. An oily base, comprising an acyl acidic amino acid monosilicone monosterol ester according to claim 1.

12. An oily base according to claim 11, further comprising an acyl acidic amino acid disilicone ester of formula (VIII):

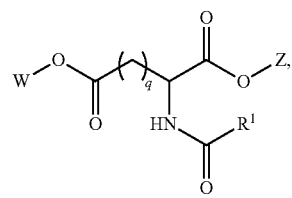

(VIII)

wherein $R^1$ represents a linear or branched hydrocarbon group of 1 to 30 carbon atoms, q is 1 to 2, and Z and W are each independently represented by formula (IX):

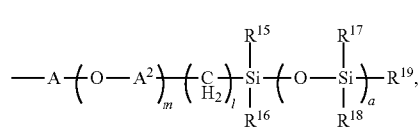

(IX)

wherein A and $A^2$ are each selected from linear or branched alkylene groups of 1 to 12 carbon atoms; l is an integer of 0 to 2; m is an integer of 0 to 10, and $R^{15}$, $R^{16}$, $R^{17}$, $R^{18}$, and $R^{19}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and a represents a number of from 2 to 10,000.

13. A process for producing a composition that contains an acyl acidic amino acid monosilicone monosterol ester, said process comprising:

mixing at least one acyl acidic amino acid, at least one carbinol-modified silicone, and at least sterol, to obtain a mixture; and esterifying said mixture in the presence of an acidic catalyst.

14. A process according to claim 13, wherein said esterifying is performed in the presence of a higher alcohol.

15. A composition obtained by a process according to claim 13.

16. A composition according to claim 15, wherein said composition has a viscosity of 10 to 600 mPa·s.

17. A composition according to claim 15, wherein said composition has a viscosity of 50 to 500 mPa·s.

18. An acyl acidic amino acid disilicone ester of formula (VIII):

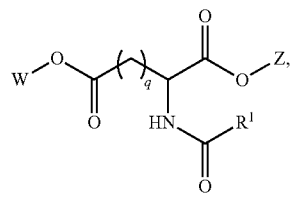

wherein $R^1$ represents a linear or branched hydrocarbon group of 1 to 30 carbon atoms, q is 1 to 2, and Z and W are each independently a group represented by formula (IX):

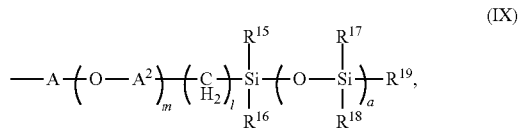

wherein A and $A^2$ are each selected from linear or branched alkylene groups of 1 to 12 carbon atoms; l is an integer of 0 to 2; m is an integer of 0 to 10, $R^{15}$, $R^{16}$, $R^{17}$, $R^{18}$, and $R^{19}$ each independently represent a hydrogen atom, a hydroxyl group, a substituted or unsubstituted alkoxy group of 1 to 30 carbon atoms, a substituted or unsubstituted alkyl group of 1 to 50 carbon atoms, an aralkyl group of 7 to 21 carbon atoms, or a substituted or unsubstituted aryl group of 6 to 20 carbon atoms, and a represents a number of from 2 to 10,000.

* * * * *